US012695850B2

(12) United States Patent
Gausserand et al.

(10) Patent No.: US 12,695,850 B2
(45) Date of Patent: Jul. 28, 2026

(54) METHOD AND SYSTEM FOR RECORDING AND TRANSMITTING IMAGES OF A MEDICAL FACILITY, ESPECIALLY IMAGES OF AN OPERATING ROOM

(71) Applicant: MEDINBOX, Toulouse (FR)

(72) Inventors: Nicolas Gausserand, Toulouse (FR); Sami Chidiac, Toulouse (FR)

(73) Assignee: MEDINBOX, Toulouse (FR)

( * ) Notice: Subject to any disclaimer, the term of this patent is extended or adjusted under 35 U.S.C. 154(b) by 0 days.

(21) Appl. No.: 18/919,854

(22) Filed: Oct. 18, 2024

(65) Prior Publication Data

US 2025/0133190 A1 Apr. 24, 2025

(30) Foreign Application Priority Data

Oct. 20, 2023 (EP) ..................................... 23306840

(51) Int. Cl.
| | |
|---|---|
| *H04N 7/18* | (2006.01) |
| *G06T 3/4053* | (2024.01) |
| *G06T 5/80* | (2024.01) |
| *G06V 20/50* | (2022.01) |
| *G06V 20/60* | (2022.01) |
| *G06V 30/19* | (2022.01) |
| *G16H 40/20* | (2018.01) |

(52) U.S. Cl.
CPC ........... *H04N 7/183* (2013.01); *G06T 3/4053* (2013.01); *G06T 5/80* (2024.01); *G06V 20/50* (2022.01); *G06V 20/60* (2022.01); *G06V 30/19* (2022.01); *G16H 40/20* (2018.01); *G06T 2200/24* (2013.01); *G06T 2207/30004*

(2013.01); *G06T 2207/30204* (2013.01); *G06V 2201/02* (2022.01); *G06V 2201/03* (2022.01)

(58) Field of Classification Search
CPC ......... H04N 7/183; G06T 3/4053; G06T 5/80; G06T 2200/24; G06T 2207/30004; G06T 2207/30204; G06V 20/50; G06V 20/60; G06V 30/19; G06V 2201/02; G06V 2201/03; G06V 10/225; G06V 10/247; G06V 20/52; G06V 20/635; G06V 10/235; G06V 30/10; G16H 40/20; G08B 13/19686
USPC ......................................................... 348/143
See application file for complete search history.

(56) References Cited

U.S. PATENT DOCUMENTS

| | | | | |
|---|---|---|---|---|
| 8,996,165 B2 * | 3/2015 | Wang | .................... | A61B 5/7465 |
| | | | | 348/14.02 |
| 9,001,208 B2 * | 4/2015 | Yasutake | .......... | H04N 21/42224 |
| | | | | 348/143 |
| 10,311,251 B2 * | 6/2019 | Singh | .................. | G06F 21/6263 |
| 11,682,225 B2 * | 6/2023 | Pribble | .................. | G06V 10/20 |
| | | | | 382/199 |

(Continued)

OTHER PUBLICATIONS

Extended Search Report issued on Jan. 6, 2024, in corresponding European Application No. 23306840.2, 8 pages.

(Continued)

*Primary Examiner* — John W Miller
*Assistant Examiner* — Omer Khalid
(74) *Attorney, Agent, or Firm* — Maier & Maier, PLLC

(57) ABSTRACT

A method and a system which may allow recording and transmitting an image of a display of a monitor positioned in a room of a medical facility, especially in an operating room.

12 Claims, 12 Drawing Sheets

(56)    References Cited

U.S. PATENT DOCUMENTS

2007/0280554 A1*  12/2007  Chernichenko ......... G06T 7/536
                                                    382/275
2020/0372180 A1   11/2020  Venkataraman et al.
2020/0373002 A1*  11/2020  Kadambi .............. G16H 30/40

OTHER PUBLICATIONS

Kim, et al., "Tele-monitoring system for intensive care ventilators in isolation rooms", Scientific Reports, Sep. 14, 2023, Nature Portfolio, vol. 13, Article No. 15207, 10 pages.
Yue, et al., "Image super-resolution: The techniques, applications, and future", Signal Processing, 2016, Elsevier, vol. 128, pp. 389-408.
Morris, et al., "Clearspeech: A Display Reader for the Visually Handicapped", IEEE Transactions On Neural Systems and Rehabilitation Engineering, Dec. 2006, IEEE, vol. 14, No. 4, pp. 492-500.

* cited by examiner

METHOD AND SYSTEM FOR RECORDING AND TRANSMITTING IMAGES OF A MEDICAL FACILITY, ESPECIALLY IMAGES OF AN OPERATING ROOM

BACKGROUND

Telecommunication technologies are increasingly used in the medicine area. Many practitioners now adapt their practice to allow virtual consultations for their patients.

However, the technology is not always adapted to the usages in medical facilities, especially in operating rooms.

The present disclosure improves the current situation.

DETAILED DESCRIPTION

Figure 1:
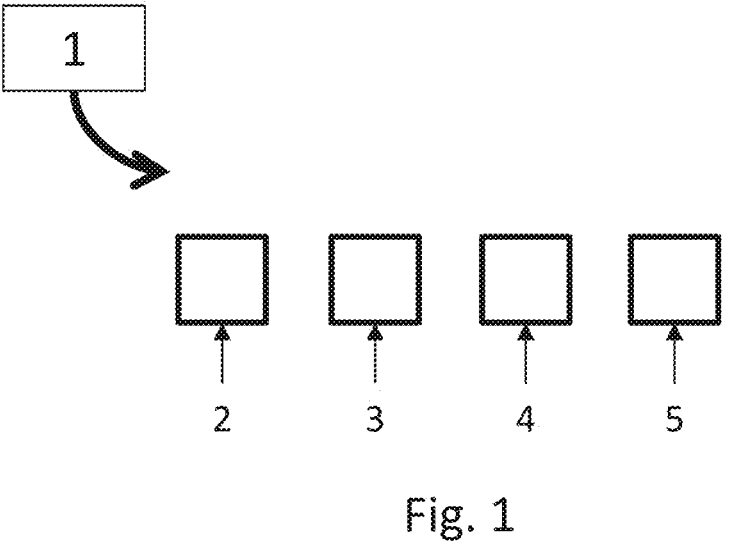
FIG. 1 illustrates schematically an example of a system according to the present disclosure.

The disclosure applies to a method and a system which may allow recording and remotely transmitting an image displayed on a health monitor in a medical facility environment, especially in an operating room.

A monitor corresponds to a display or a screen displaying a video source received from a medical device. The medical device corresponds to a device acquiring a health data related to a patient. In some examples, a monitor may display a plurality of video sources, the plurality of video sources may for example be received by the monitor from several medical devices. A monitor simultaneously displaying several video sources received from different medical devices is widely used in operating rooms for aggregating, in a same display, the different health data of a patient acquired by the medical devices.

A medical facility may for example correspond to a clinic or a hospital. An operating room may be defined as a room in which surgical operations, cardiac or vascular operations are performed. The operating room may sometimes be referred as interventional room or operating theater. An operating room is especially equipped by an operating room manufacturer providing an operating suite comprising the different medical devices.

The system and the method may for example allow recording and transmitting live images of a health monitor displaying health data related to a patient in a room such that a practitioner can remotely monitor these data from a different room, or such that a practitioner can review the data displayed on the health monitor. Another practical example of the system and the method according to the present disclosure can be applied when performing a surgical intervention on a patient. In this case, the monitors displayed in the operating room can be remotely supervised by practitioners positioned outside of the operating room or can be reviewed, after the intervention for any needs, especially pedagogic or legal needs.

It should be noted that the health monitors in medical facilities are provided by different manufacturers which use different technologies. Not all the monitors present dedicated inputs for connecting wires allowing recovering the images displayed on the monitors. Moreover, for the monitors which present dedicated inputs to recover the images, the connectors of these inputs as well as the ease of access to these connectors vary between the manufacturers. Most of the time, an operator of the monitor's manufacturer must intervene to prepare access to the connectors, for example by installing an adapter on the connectors before plugging the wires, or by identifying the correct network connection in a patch panel. Once plugged, the operator must configure the system to recover the good sources and for transmitting the good images. This type of intervention also requires a validation of the medical facility and of the operating room manufacturer. Hence, even for a monitor in which the connectors can be easily accessed, a validation step and a configuration step requiring a technical expertise are still needed. That is, recovering the images displayed by the monitor using a physical connection (i.e. wires) is time consuming, requires expertise, and could be expensive.

The inventors have cleverly found out that using a camera for capturing an image of a display of the monitor for recording this image can overcome at least part of these issues. Indeed, having a camera capturing an image of the display of the monitor does not imply a physical connection with the monitor to acquire the image. That is, it is no longer needed to have an intervention of an operator to access the connectors of a monitor for recovering the images displayed by the monitor.

However, the inventors have noticed that a camera filming a health monitor for recording and transmitting images of the display of the monitor leads to other types of issues. Although using a camera facilitates the recovering of the images displayed on a monitor with respect to a physical connection to the monitor, the quality of the images of the display of the monitor recorded by the camera is not equivalent to the quality of the images obtained by connecting the monitor with wires. For example, using smartphones for filming the monitor may lead to poor quality video and is not convenient for the person carrying the smartphone.

The solution disclosed in the present disclosure allows, in addition of facilitating the recovering of the images displayed on a monitor with respect to a physical connection to the monitor, at least mitigating, eventually suppressing, the difference in quality between the images displayed on the monitor and recorded by a camera and the images obtained by a physical connection to the monitor. In some examples, the quality of the images of the display of the monitor recorded by the camera may even be improved with respect to the ones obtained by a physical connection to the monitor. Moreover, the solution disclosed in the present disclosure can be deployed with no or reduced expertise and with no or significantly reduced validation process compared to a connection with the monitor using wires.

In other words, the solution presented by the present disclosure offers a system and a method that can be deployed by a non-technical person in a medical facility, especially in an operating room, ensuring recording and transmitting successive images (i.e. a video signal) of a monitor having a good quality, in real-time, without requiring any wired connection. In some examples, the solution may also be able to recognize and treat the images so that the solution can be used for different needs, such as anonymizing, streaming it online or inviting a third party to collaborate.

An example of a system 1 whereby a method which may allow recording and remotely transmitting an image of a monitor can be implemented is described below with reference to FIG. 1. Examples of these methods are described in reference to FIGS. 7 to 20. These examples of methods may be applied on successive images in real-time for transmitting a live video of the images displayed on the monitor.

The system 1 comprises a camera 2, a controller 3 (or computing system), a memory 4 (or computer-readable storage), and a communication unit 5. The controller 3 has access to a memory 4 such that the controller 3 may use the data stored in the memory 4.

The memory 4 may be encoded with instructions executable by a controller such as the controller 3 causing the controller to perform any of the examples of methods described 5 in this disclosure. The memory 4 may also store the images acquired by the camera.

A memory 4, or a computer-readable storage medium, according to this disclosure may be any electronic, magnetic, optical or other physical storage device that stores executable instructions. The memory 4 or computer-readable storage may be, for example, a Random Access Memory (RAM), a storage drive, and optical disk, and the like. Storage or memory may include any electronic, magnetic, optical or other physical storage device that stores executable instructions as described hereby.

The communication unit 5 is configured to transmit an image or a plurality of images (a video) to a receiving device (not represented). The communication unit 5 may be hardware or software implemented. The communication unit 5 may transmit an image to a receiving device using a wireless technology or using wires.

Figure 2:
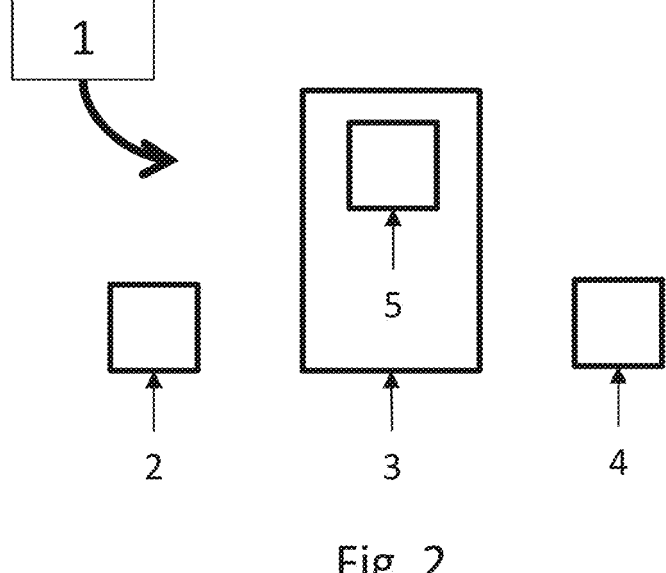
FIG. 2 illustrates schematically another example of a system according to the present disclosure.

In some examples, the communication unit 5 may for example be implemented in the controller 3. These examples are schematically illustrated in FIG. 2.

The receiving device (not represented) may be a device external from the system 1. The receiving device may especially be positioned in another room (i.e. in another location) than the room in which the camera 2 is positioned for acquiring the images. The receiving device may correspond to a dedicated memory (not represented) for storing the successive images such that a video of the monitor can be reviewed.

Figure 3:
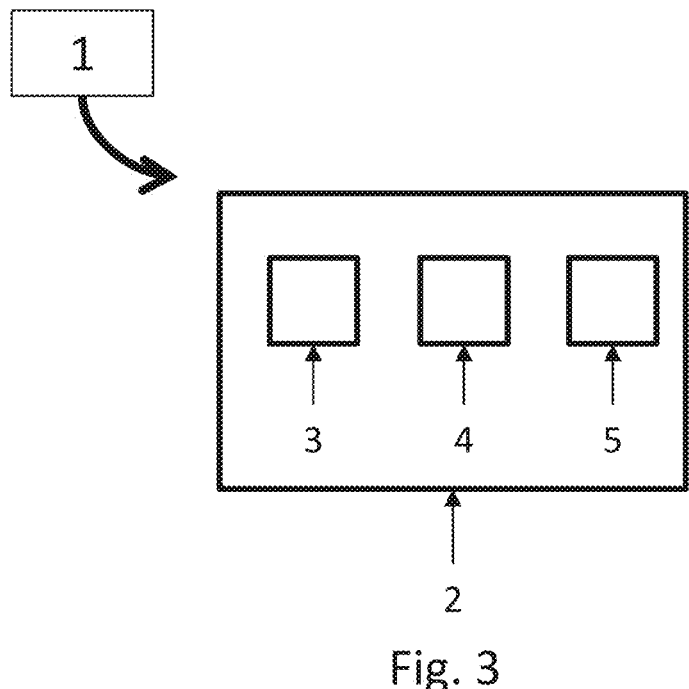
FIG. 3 illustrates schematically yet another example of a system according to the present disclosure.

In some examples, the controller 3, the memory 4, and the communication unit 5 (integrated or not in the controller 3) may be integrated into the camera 2. In these examples, the system 1 may comprise solely the camera 2. These examples are schematically illustrated in FIG. 3.

In some examples, the camera 2 and the controller 3 are distinct from each other and the images acquired by the camera 2 are transmitted to the controller 3 by transmitting the data using wires or by transmitting the data using a protocol of telecommunication, i.e. using a wireless communication medium. In these examples, the controller 3 may be integrated in a computer (laptop or desktop computer).

Figure 4:
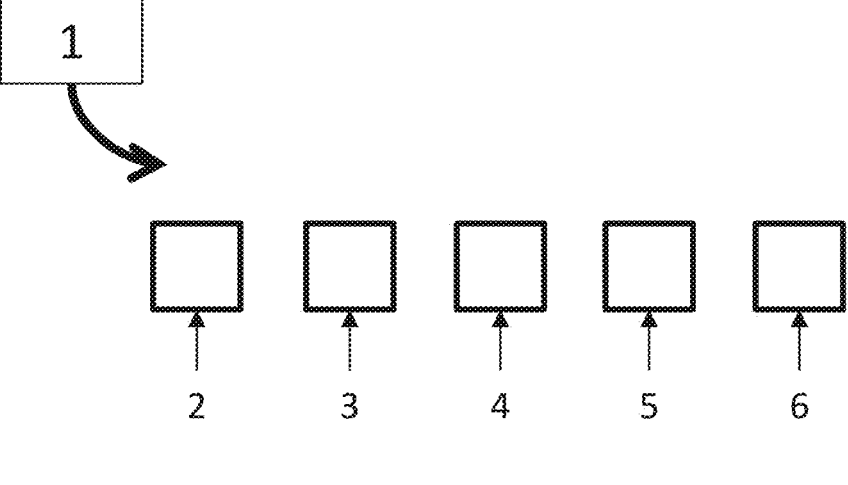
FIG. 4 illustrates schematically yet another example of a system according to the present disclosure.

In some examples, the system 1 may comprise a mobile device 6. These examples are schematically illustrated in FIG. 4.

The mobile device may for example comprise a wheel, or a plurality of wheels. The mobile device 6 may for example correspond to a flight case 61.

Figures 5, 6, 7:
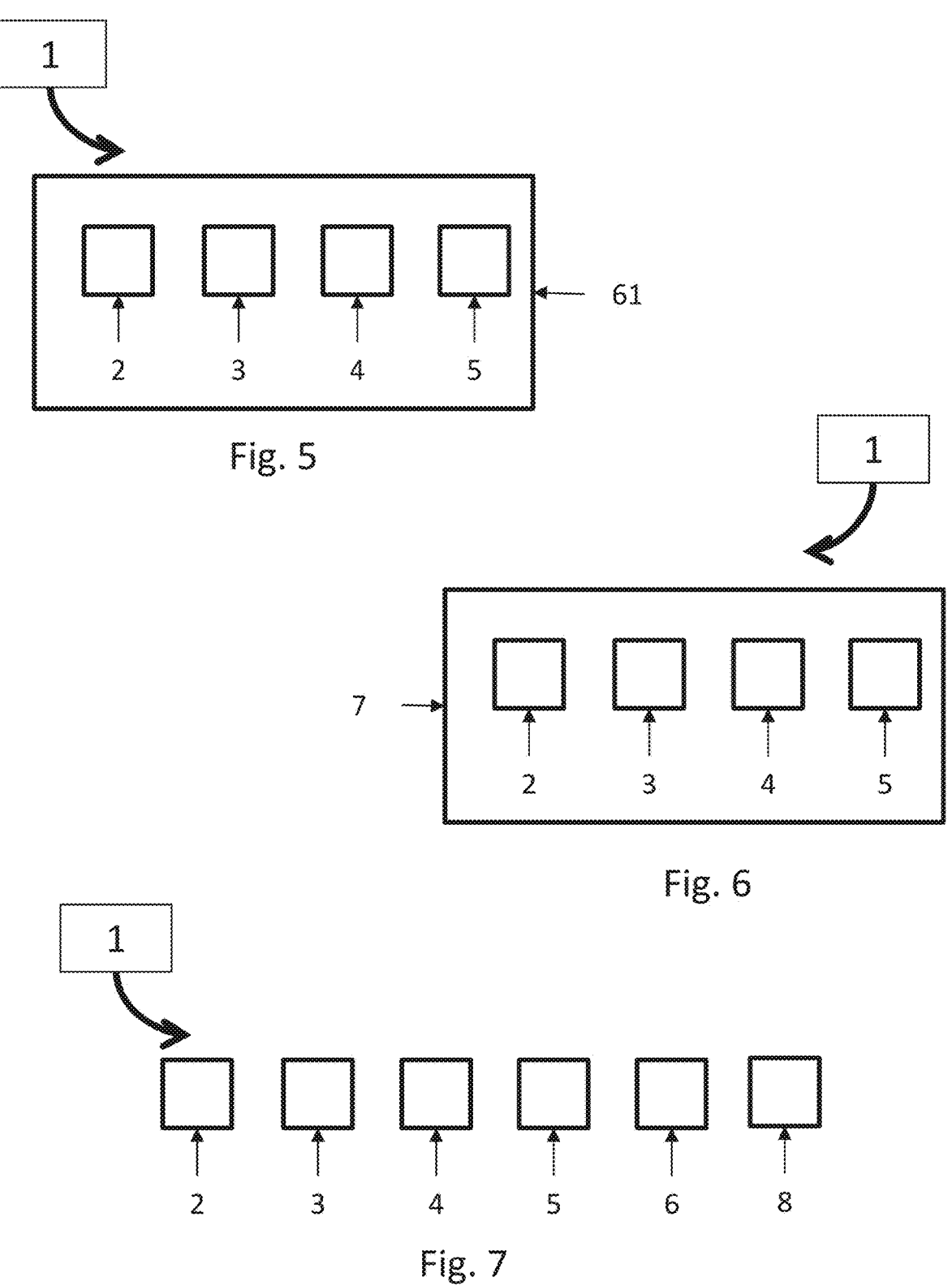
FIG. 5 illustrates schematically yet another example of a system according to the present disclosure.
FIG. 6 illustrates schematically yet another example of a system according to the present disclosure.
FIG. 7 illustrates schematically yet another example of a system according to the present disclosure.

In examples wherein the system 1 comprises a flight case 61 and wherein the controller 3 is integrated in a computer, the computer can be removably connected to the flight case such that the computer can be easily transported to a room of a medical facility, especially in the operating room. In these examples, the flight case may comprise a first housing sized or shaped to receive the computer and a second housing sized or shaped to receive the camera 2. Hence, in these examples, the system 1 takes the form of a flight case 61 which can easily be moved to a room of a medical facility, especially to an operating room to be deployed, and which secures the transport of the computer and the camera 2. These examples are schematically illustrated in FIG. 5.

In some examples, the system may comprise a backpack 7. In examples wherein the system 1 comprises a backpack 7 and wherein the controller 3 is integrated in a computer, the backpack 7 may comprise a first housing sized or shaped to receive the computer and a second housing sized or shaped to receive the camera 2. Hence, in these examples, the system 1 takes the form of a backpack which can easily be carried by a person to a room of a medical facility, especially to an operating room to be deployed, and which secures the transport of the computer and the camera 2. These examples are schematically illustrated in FIG. 6.

In some examples, the system 1 may comprise a microphone 8 configured to acquire an audio. In these examples, the system 1 may both acquire an audio in the operating room and capture an image (or a video) of a display of a monitor in the operating room. These examples are schematically illustrated in FIG. 7.

Examples of a computer-implemented method 100 which may allow recording and remotely transmitting an image of a monitor is described below with reference to FIGS. 8 to 20. The monitor may correspond to a health monitor, for example positioned in a medical facility environment, especially in an operating room. It should be noted that the examples of methods 100 below are described for an image but can obviously be applied for a video, which corresponds to a plurality of images acquired at a given frequency.

The image of the monitor comprises a display or a screen of the monitor. One of the purposes of the example methods 100 is to remotely transmit a display of a monitor, acquired on a monitor positioned in a room of a medical facility, especially in an operating room, outside of the operating room.

It should be noted that the example of methods 100 illustrated in the figures are merely an illustration of examples of process representing, by means of blocks, the various operations that may be included in the process and described in the remainder of the document. As such, these illustrations do not reflect any seriality between the blocks. In other words, the blocks described with reference to the methods 100 illustrated in the figures are not necessarily implemented one after the other, and may in particular be implemented in a different order from the ones shown in the figures, or be implemented in parallel. Similarly, it is not necessary for each block to be implemented once before that a same block could be performed a second time. The frequency of the implementation of each block is specific to it and is not necessarily linked to the implementation of the other blocks.

Figure 8:
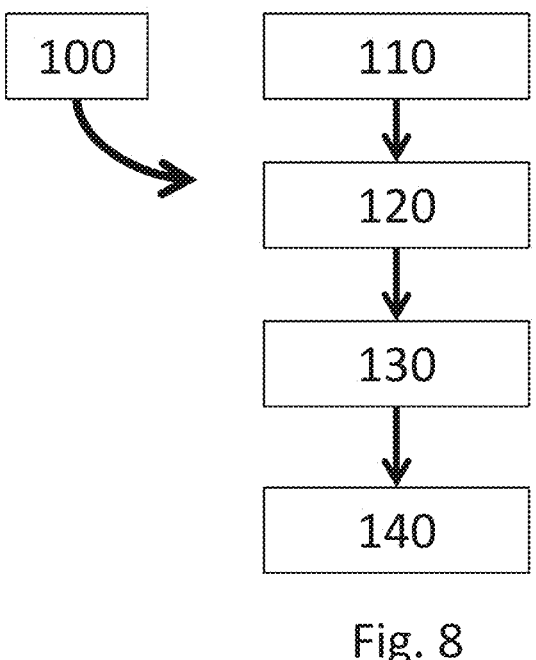
FIG. 8 illustrates schematically an example of a method according to the present disclosure.

With reference to FIG. 8, the example of method 100 comprises, as illustrated in block 110, obtaining an image of a room of a medical facility, especially of an operating room comprising a monitor. The image may be acquired by a camera. The image of the room of a medical facility, especially of the operating room may for example be acquired by the camera 2. The obtained image comprises a monitor, especially a display of the monitor. The camera may therefore be positioned relatively to the monitor such that the captured image comprises a display of the monitor.

As illustrated in block 120, the method 100 comprises detecting the monitor in the image. In some examples, the method 100 may comprise detecting a screen (or a display) of the monitor in the image.

As illustrated in block 130, the method 100 comprises performing a perspective transformation of the detected monitor in the image for mitigating a perspective distortion of the detected monitor. In some examples, performing a perspective transformation of the detected monitor corresponds to performing a perspective correction method on the display of the detected monitor in the image.

The inventors have noticed that an obtained image acquired by a camera in a room of a medical facility, especially in an operating room may comprise a perspective distortion depending on the position and orientation of the camera relatively to the monitor. This effect degrades the quality of the monitor acquired in the image. Indeed, in a room of a medical facility, especially in an operating room, the camera acquiring the images cannot be positioned at any position. In many situations, the camera cannot be positioned in front of the monitor where the perspective distortion is reduced. Indeed, in these situations, the camera may disturb the practitioners in the operating room for performing the medical act, which is not a satisfying solution.

The inventors have further noticed that even in a theoretical situation where the camera would be perfectly positioned and oriented relatively to the monitor without disturbing the practitioners of the operating room, the monitor must stay completely immobile to continue to acquire images with the camera which present no perspective distortion. In practice, monitors in the operating room must be moved in response to many situations. An example of situation is to let the space usually occupied by the monitor in the operating room to a practitioner for performing a medical act on a patient. Another example of situation is when the monitor is moved and/or oriented to face a practitioner to help the practitioner to visualize a medical act, for example to supervise the act of another practitioner or to directly help the practitioner to perform the act. The latter situation can specifically happen when the monitor in the operating room to be recorded corresponds to the monitor aggregating and displaying multiple video sources from different medical devices in the operating room. This monitor is generally mounted on an articulated arm such as the monitor can be moved and be oriented according to the needs. That is, even having a perfect position of the camera relatively to the monitor to be recorded is not a satisfying solution if the monitor is mobile.

Hence, the inventors have ingeniously found out that performing a perspective transformation of the monitor detected in the obtained image for mitigating a perspective distortion of the detected monitor allows increasing the quality of the monitor in the image. In fact, the quality difference between the image obtained using a physical connection with the monitor and the image of the monitor acquired by the camera without any physical connection is at least reduced and at most completely removed.

As illustrated in block 140, the method 100 comprises transmitting an image comprising the detected monitor with mitigated perspective distortion. That is, the image to be transmitted is issued from the image obtained in block 110, and amended based on the perspective transformation such that the image to be transmitted comprises the monitor detected in block 120 with mitigated perspective distortion.

The image to be transmitted may for example be sent to a receiving device. As previously explained, the receiving device may for example correspond to a dedicated memory (not represented) for storage purposes which allows having access to the image (or the successive images in case of a video) after their transmission. The receiving device may be positioned outside of the room of the medical facility, especially outside of the operating room such that the image of the monitor may be displayed in a remote location, and may especially be displayed in real time in a remote location during an intervention.

That is, the example of method 100 according to the present disclosure allows transmitting an image of a monitor comprising a display of a monitor positioned in a room a room of a medical facility, especially in an operating room. The method does not imply the intervention of a technical operator, i.e. can be implemented by a person with reduced or no technical expertise, and can be implemented with reduced or no validation process, compared to a method based on a physical connection of the monitor using wires. Moreover, the image to be transmitted to the receiving device can be obtained based on an image acquired by a camera positioned in a wide range of positions in the room of the medical facility, especially in the operating room while significantly keeping the same quality when transmitted.

Other blocks may optionally be integrated into the example of method 100 described with reference to FIG. 8 and are presented in the remainder of the present disclosure. Each optional block may especially be integrated into the example method 100 of FIG. 8 alone or in combination with one or more of the other blocks, unless the contrary is expressly stipulated.

Figure 9:
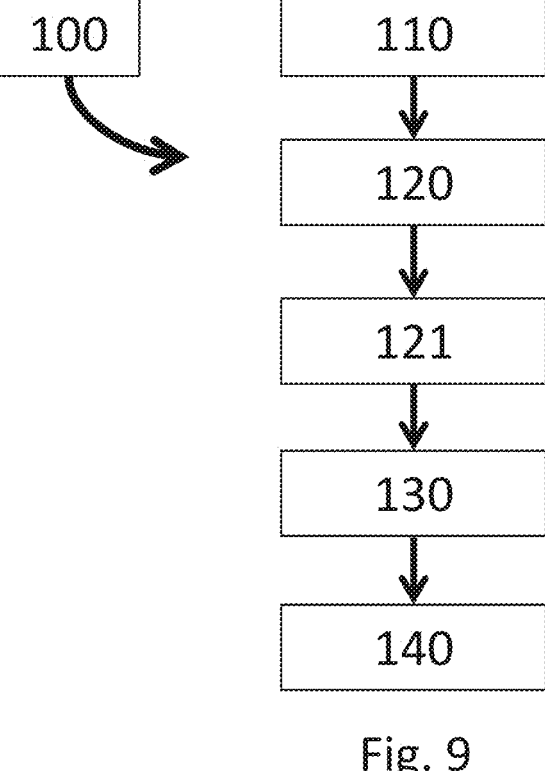
FIG. 9 illustrates schematically another example of a method according to the present disclosure.

In some examples, the block 120 of detecting the monitor in the image obtained in block 110 may comprise a block 121 of determining a quadrilateral, or a quadrilateral shape, in the image. These examples are schematically illustrated in FIG. 9. In these examples, the quadrilateral determined in the block 121 may correspond to the detected monitor. Indeed, the monitors positioned in a room of a medical facility, for example in an operating room, especially their respective display, present a rectangular shape. However, the perspective distortion of the image leads to a distortion of the rectangular shape of the monitor to form a quadrilateral shape. Hence, the example method 100 may detect the monitor in the room of the medical facility, especially in the operating room by determining a quadrilateral shape in the image.

In some examples, a quadrilateral corresponding to a monitor may be discriminated compared to other quadrilaterals determined in the image based on at least one of a colorimetry of the pixels of the quadrilateral, of a size of the quadrilateral, of a text detected in the quadrilateral, or of a height of the quadrilateral.

In some examples wherein the example method 100 comprises the block 121 of determining a quadrilateral, or a quadrilateral shape, in the image, several options may be implemented for determining the quadrilateral.

Figure 10:
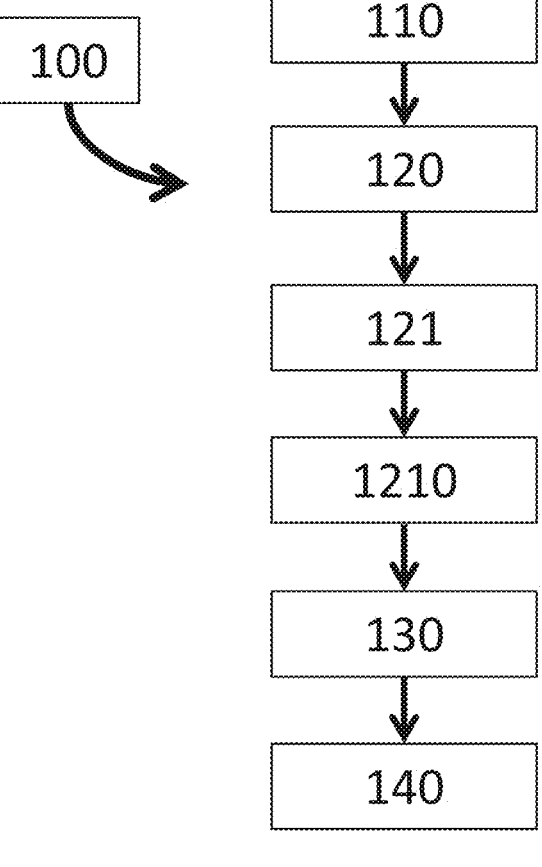
FIG. 10 illustrates schematically yet another example of a method according to the present disclosure.

A first option for determining a quadrilateral in the image, schematically illustrated in FIG. 10 by the block 1210, may be to determine the quadrilateral in the image obtained in block 110 based on a quadrilateral detection method. A quadrilateral detection method may for example be based on a Hough transform technique. Hence, in this option, the monitor, which corresponds to the determined quadrilateral, is automatically detected.

Figure 11:
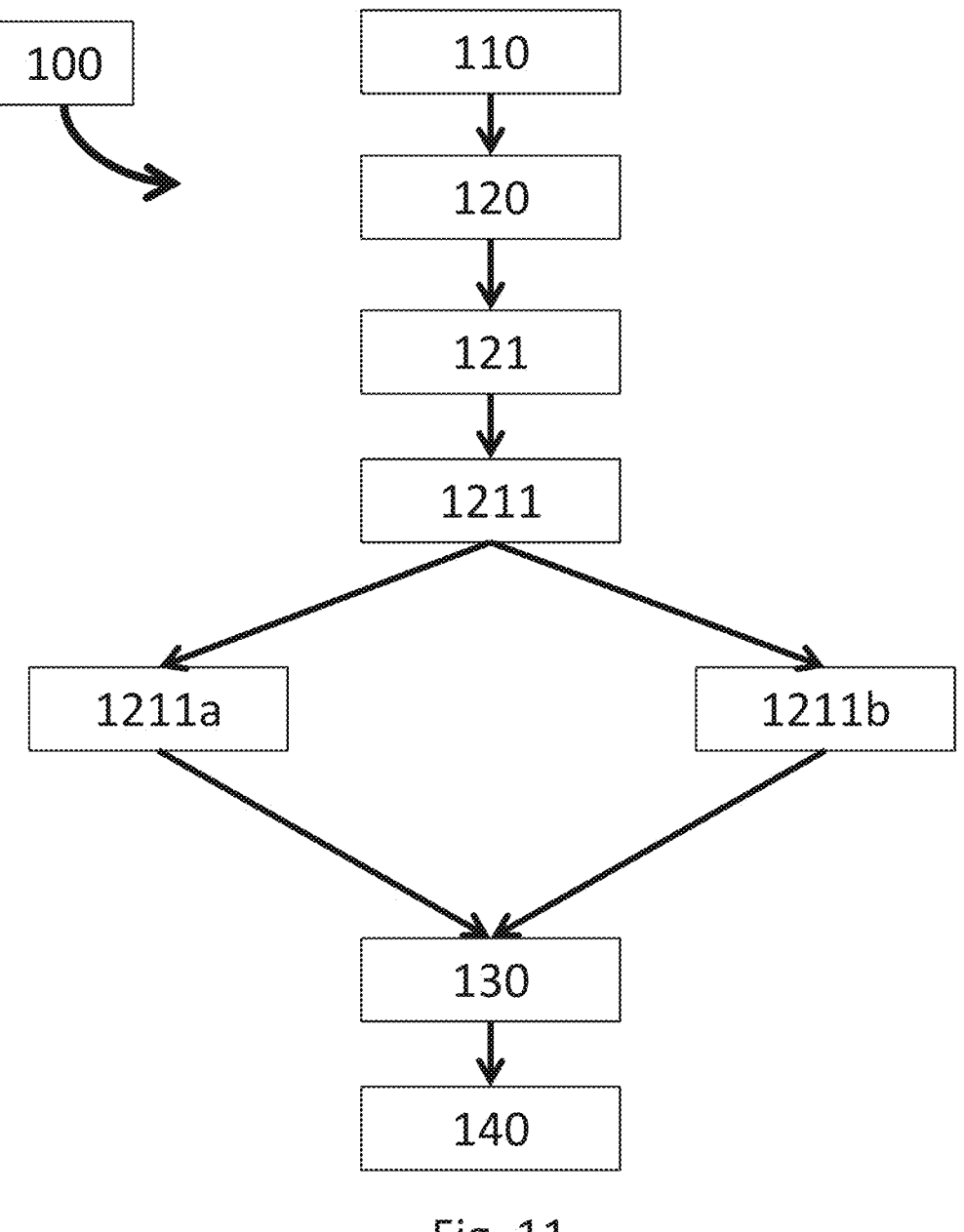
FIG. 11 illustrates schematically yet another example of a method according to the present disclosure.

A second option for determining a quadrilateral in the image, schematically illustrated in FIG. 11 by the bloc 1211, may comprise determining four corners associated to the quadrilateral. In this second option, determining the four corners associated to the quadrilateral may comprise two alternatives:

1) receiving four points of the image, acquired by a man-machine interface, identifying the four corners of the quadrilateral corresponding to the four corners of the monitor to be detected in block 120; or
2) identifying four predetermined markers in the image, each of the markers corresponding to a respective corner of the quadrilateral which corresponds to the four corners of the monitor to be detected in block 120.

In the first alternative of the second option, schematically illustrated in the FIG. 11 by the bloc 1211a, a user may for example select the four corners of the quadrilateral, which correspond to the four corners of the monitor in the image, with a computer mouse or a touchscreen. In this first alternative, the monitor is not automatically detected.

In the second alternative of the second option, schematically illustrated in the FIG. 11 by the bloc 1211b, the monitor to be detected comprises predetermined markers in the four corners of its display. The predetermined markers can be positioned in the four corners of the display of the monitor by a person before deploying the system 1. Then, these examples of method 100 are able to detect the four predetermined markers in the image obtained in block 110 using image processing and to determine that each of the marker corresponds to a respective corner of the quadrilateral, the quadrilateral corresponding to the monitor to be detected in block 120. In this second alternative, the monitor is automatically detected.

In some examples of the method 100 comprising the block 121 wherein the monitor is detected by determining a quadrilateral in the image, the block 130 of performing a perspective transformation of the detected monitor in the image for mitigating a perspective distortion of the detected monitor may comprise:

applying a perspective distortion correction method to the quadrilateral corresponding to the detected monitor such that the quadrilateral is transformed to a rectangle.

Figures 12, 13:
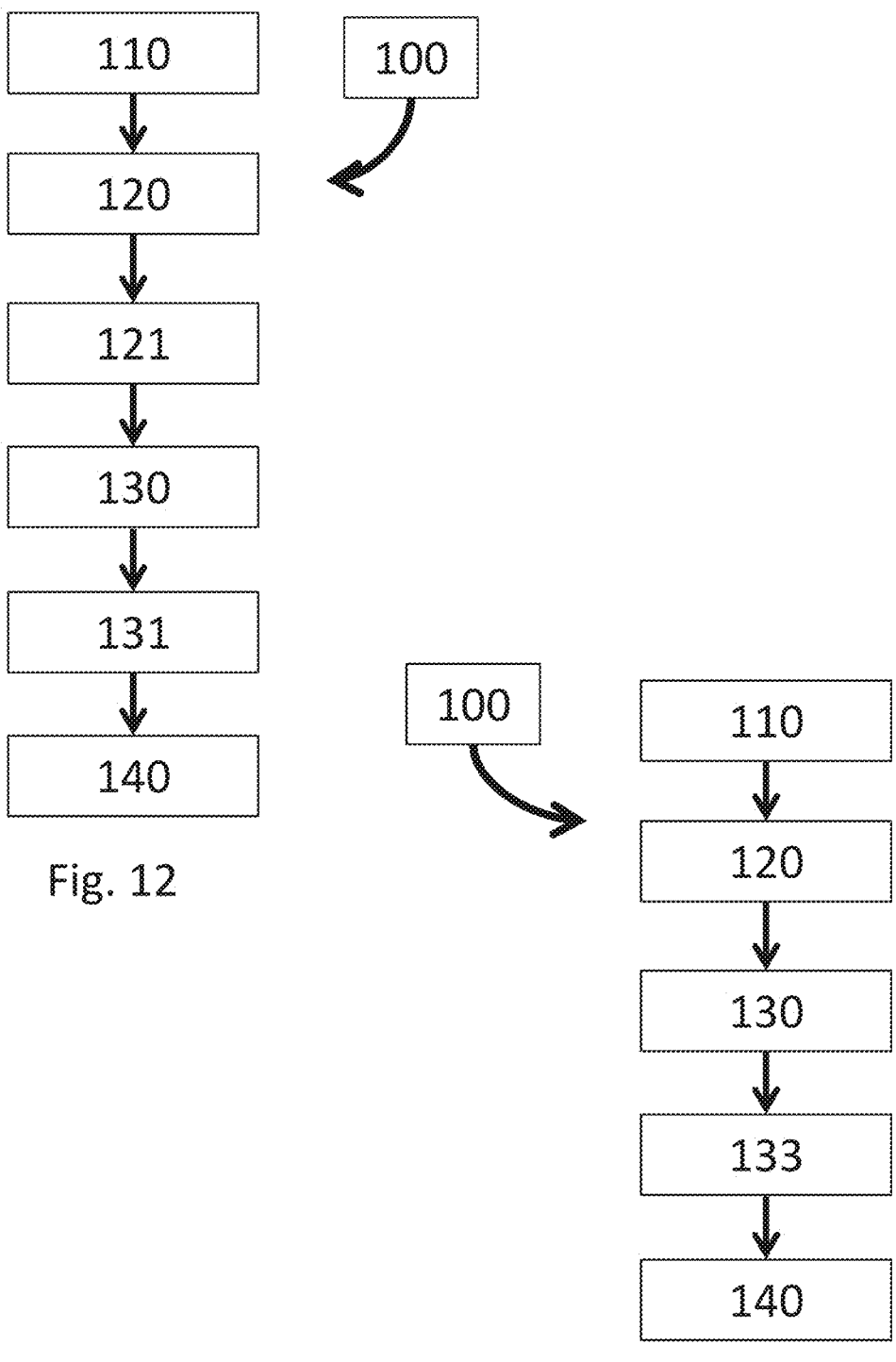
FIG. 12 illustrates schematically yet another example of a method according to the present disclosure.
FIG. 13 illustrates schematically yet another example of a method according to the present disclosure.

In other words, applying a perspective distortion correction method to the quadrilateral determined in bloc 121 allows mapping the quadrilateral of a distorted image (image obtained in block 110) to a rectangle of a corrected image. These examples are schematically illustrated in FIG. 12 by the bloc 131. A perspective distortion correction method may for example comprise determining a homography matrix or a Hough transform.

In some examples, the method 100 may further comprise a block 133 of anonymizing an image to be transmitted by masking personally identifiable information of a patient. The block 133 may preferably be implemented before the block 140 of transmitting the image such that the personally identifiable information are not transmitted to another system than the example of system 1 before being anonymized. These examples are schematically illustrated in FIG. 13.

In some examples of the method 100 comprising the block 133, anonymizing the image to be transmitted by masking personally identifiable information of a patient may comprise:

a block 134 of determining coordinates of the personally identifiable information in the image to be transmitted; and
a block 135 of applying a mask on determined coordinates of the image to be transmitted.

Figure 14:
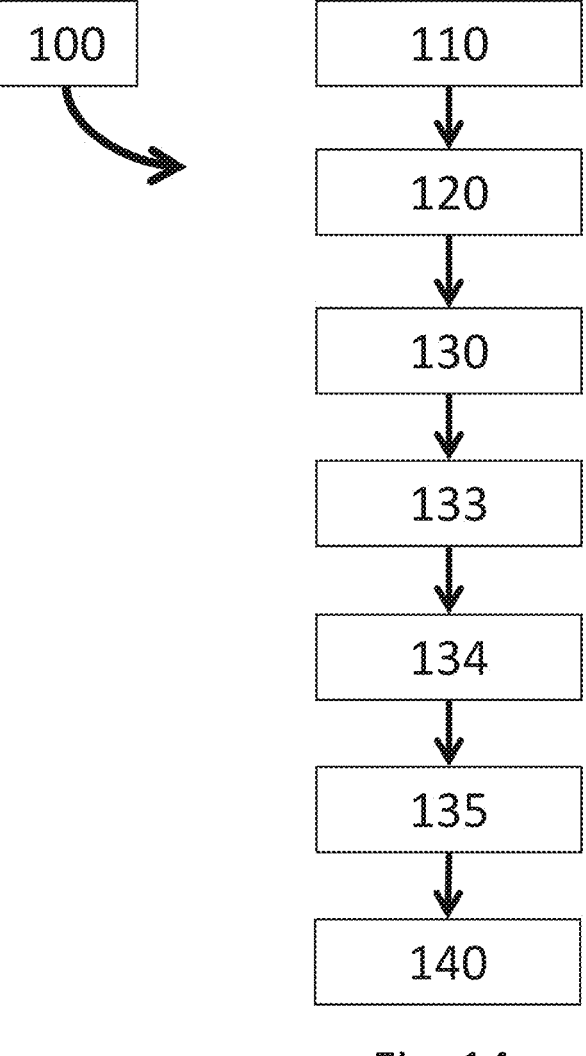
FIG. 14 illustrates schematically yet another example of a method according to the present disclosure.

These examples are schematically illustrated in FIG. 14.

A first option for determining the coordinates of the block 134 may comprise:

applying an optical character recognition method (OCR method) on the image for determining a plurality of characters;
identifying the characters corresponding to the personally identifiable information among the plurality of determined characters; and
determining the coordinates associated to the identified characters in the image to be transmitted.

Figure 15:
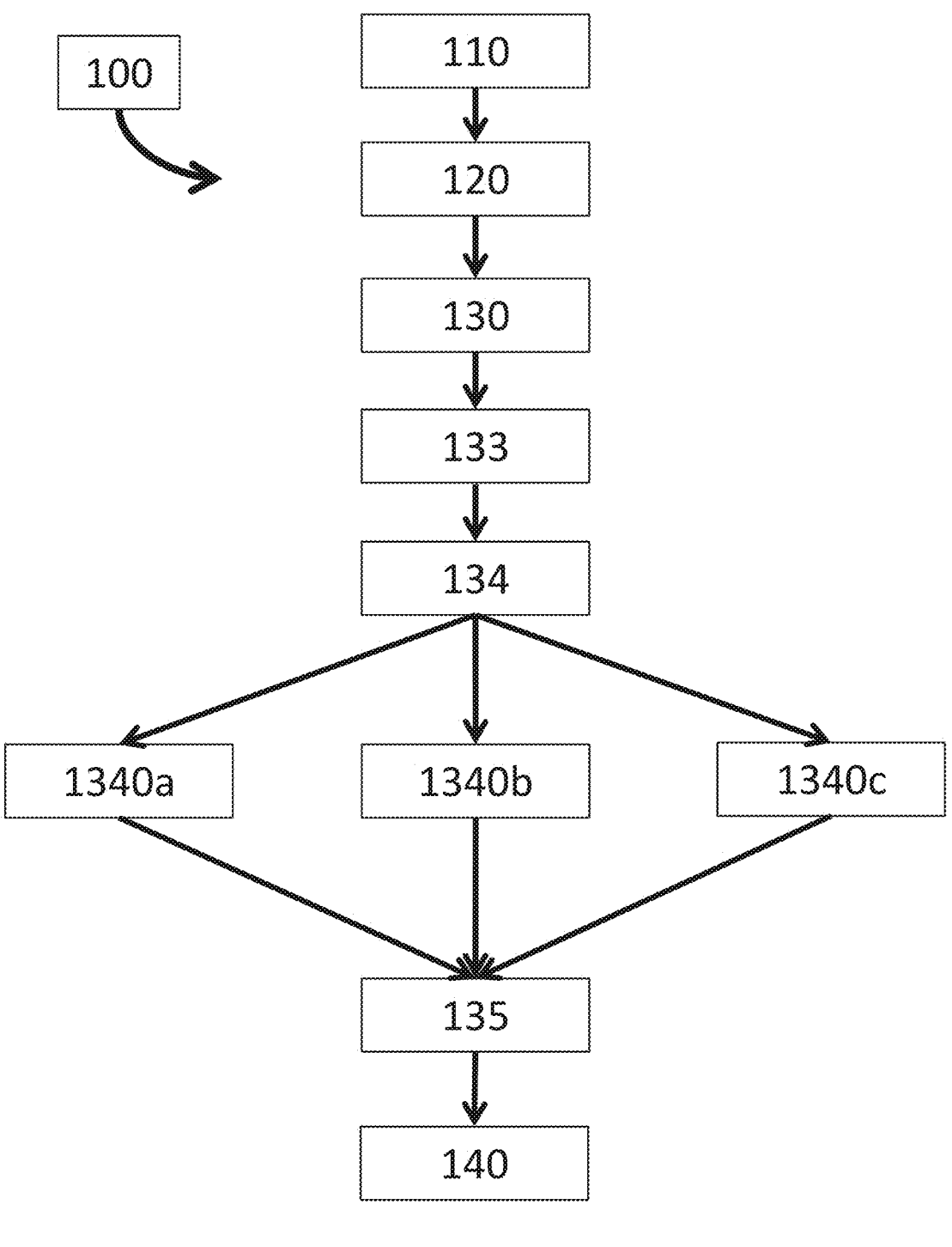
FIG. 15 illustrates schematically yet another example of a method according to the present disclosure.

This first option is schematically illustrated by the block 1340a in FIG. 15.

In some examples of the first option, identifying the characters corresponding to the personally identifiable information among the plurality of determined characters may be implemented based on a model trained using a database of personally identifiable information. The database of personally identifiable information may for example comprise text data associated with at least one of the following types of personally identifiable information: a first name, a family name, a date of birth, an address, a social security number, a national identifier, a medical record number, health information, a phone number or an email address.

A second option for determining the coordinates of the block 134 may comprise:

identifying, in the image to be transmitted, a graphical user interface (GUI); and
retrieving coordinates associated to the personally identifiable information in the identified graphical user interface.

This second option is schematically illustrated by the block 1340b in FIG. 15.

In some examples of the second option, identifying, in the image to be transmitted, a graphical user interface associated to a monitor model may be implemented based on a model, for example a convolutional neural network (CNN), trained using an image database comprising a plurality of images of graphical user interfaces, each associated to coordinates of the personally identifiable information in the GUI. In some examples, each GUI may also be associated to at least one of a medical device model or a tab of a medical device model. It should be noted that if the monitor to be recorded displayed several video sources, the image of the display of the monitor to be transmitted may previously be divided to isolate each of the video source, for example by using a straight lines detection method. Then, the operation of identifying, in the image to be transmitted, a graphical user interface (GUI) may be implemented on each of the video sources to retrieve the coordinates associated to the personally identifiable information of each video source and therefore masking all the personally identifiable information of the monitor in the image.

A third option for determining the coordinates of the block 134 may comprise:

receiving inputs from a man-machine interface associated with coordinates.

The inputs may be received based on clicks using a computer mouse or based on a touchscreen the image to be transmitted displayed on a screen, for example on a computer screen.

This third option is schematically illustrated by the block 1340*c* in FIG. 15.

Figures 16, 17:
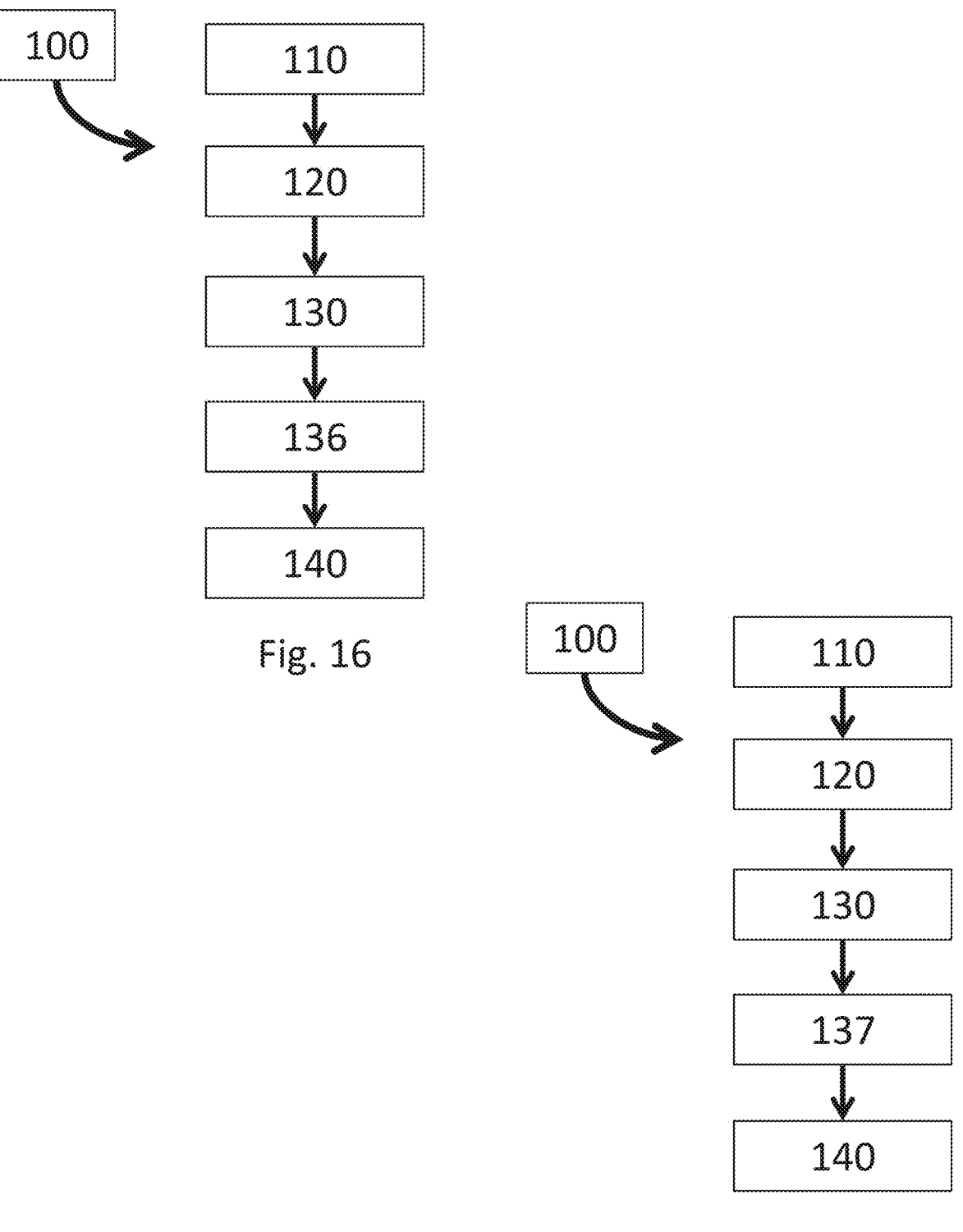
FIG. 16 illustrates schematically yet another example of a method according to the present disclosure.
FIG. 17 illustrates schematically yet another example of a method according to the present disclosure.

In some examples, the method 100 may further comprise a block 136 of cropping the image to be transmitted. In these examples, the image to be transmitted may be cropped to fit with a predetermined format, for example the format adapted to the receiving device. These examples are schematically illustrated in FIG. 16.

In some examples, the method 100 may further comprise a block 137 of adding stripes to the image to be transmitted, especially adding black stripes. In these examples, the stripes may be added to fit with a predetermined format, for example the format adapted to the receiving device. These examples are schematically illustrated in FIG. 17.

Figures 18, 19:
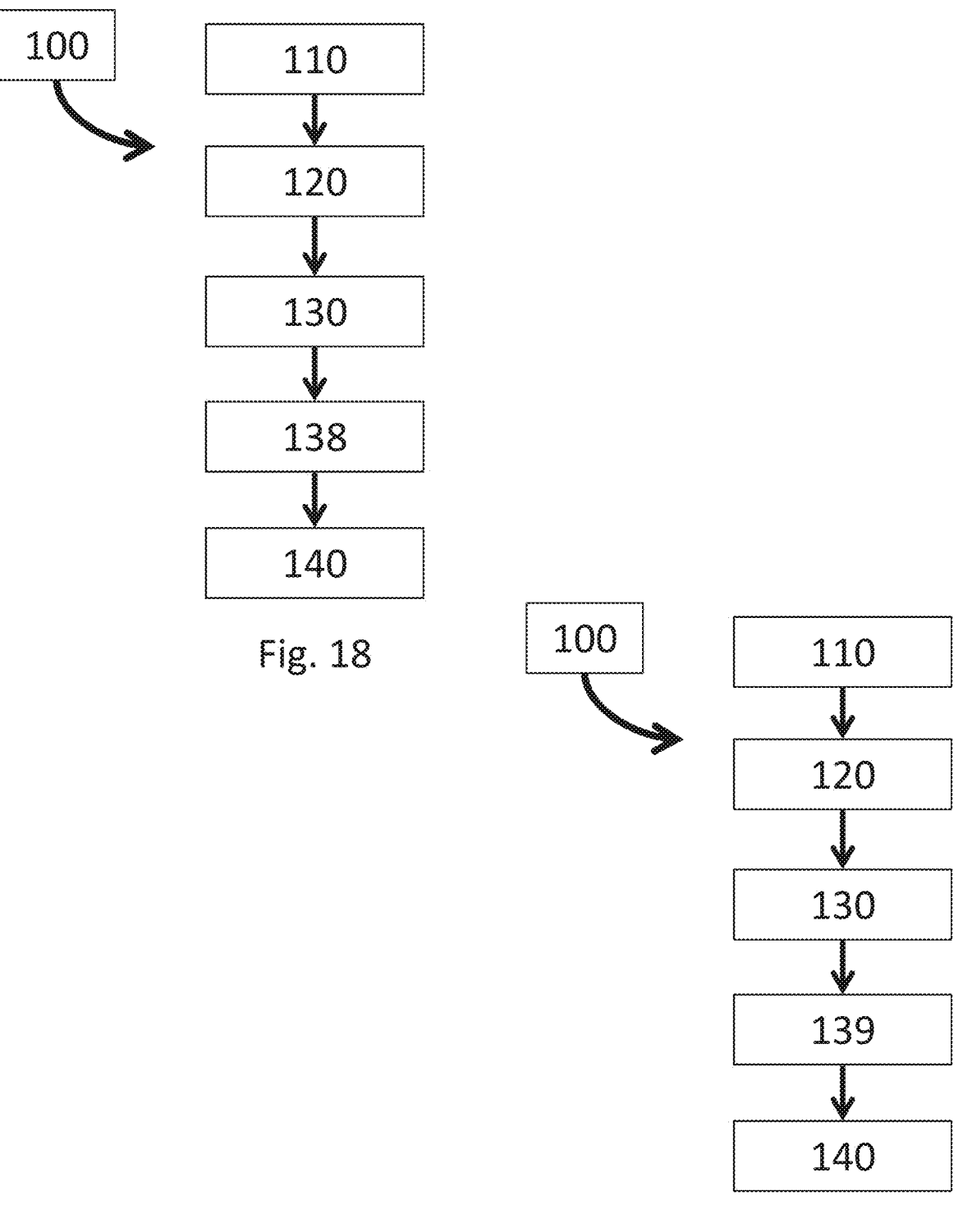
FIG. 18 illustrates schematically yet another example of a method according to the present disclosure.
FIG. 19 illustrates schematically yet another example of a method according to the present disclosure.

In some examples, the method 100 may further comprise a block 138 of improving a resolution quality of the image to be transmitted based on a super-resolution imaging method. These examples are schematically illustrated in FIG. 18. The inventors have noticed that the monitors in medical facilities, especially in operating rooms, can present low resolution since these monitors can be aged or damaged. The low resolution may render the interpretation of the information displayed on the monitor complex. Hence, improving the resolution quality of the image to be transmitted using a super-resolution imaging method could overcome this issue. In other words, in the examples of method 100 comprising the block 138, the image quality of the display of the monitor is even better than the quality of the image obtained by a physical connection to the monitor.

Figure 20:
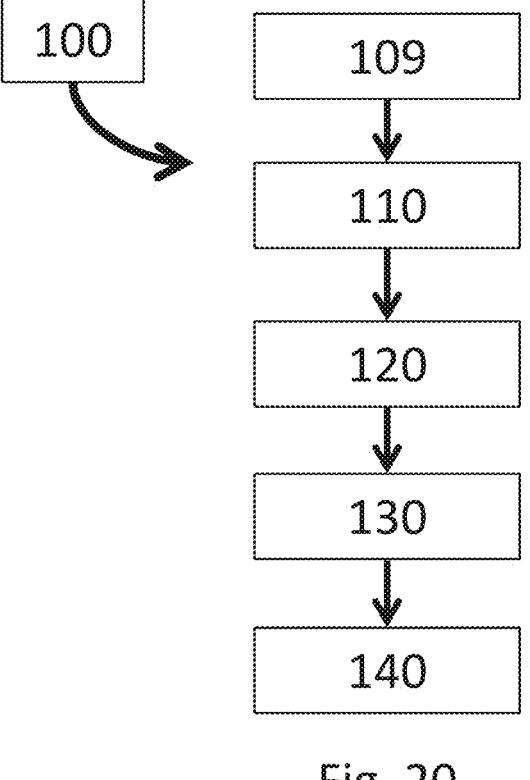
FIG. 20 illustrates schematically yet another example of a method according to the present disclosure.

In some examples, the method 100 may further comprise a block 139 of encrypting the image to be transmitted. The block 139 may preferably be implemented before the block 140 of transmitting the image such that the image to be transmitted is securely transferred to the receiving device. These examples are schematically illustrated in FIG. 20.

In some examples, the method 100 may further comprise a block 109 of positioning the camera in the room of the medical facility, especially in the operating room, wherein the camera is positioned at a distance greater than a predetermined distance threshold from the detected monitor. Indeed, when the camera is too close from the monitor to be detected, the image acquired by the camera may not comprise the whole surface of the display of the monitor. These examples are schematically illustrated in FIG. 20.

The present disclosure also presents a computer-readable storage medium comprising instructions which, when executed by at least one controller, cause the controller to carry out any one of the methods presented hereby.

The present disclosure also describes a computer program product comprising instructions which, when the program is executed by a computer, cause the computer to carry out any one of the methods hereby described.

The examples of systems and methods according to the present disclosure allows recording and transmitting an image of a display of a monitor acquired in a medical facility, especially an operating room without any wired connections. In particular, the example of systems can be easily deployed and positioned at a wide variety of positions in the room of the medical facility, especially in the operating room, while still transmitting an image of the display of the monitor with good quality, and presenting reduced disturbances for the practitioners in this room compared to system using wires. The example methods and systems according to the present disclosure may allow especially recording and live transmitting, in real-time, images of the display of the monitor with mitigated perspective distortion. In some examples, the methods and systems may anonymize the personal information indication displayed in the images to be transmitted, and may improve the quality resolution of these images based on image processing techniques. Moreover, in some examples, once the image is acquired (i.e. once the camera is positioned), all the blocks of the method 100 may be automatically implemented by the system 1 such that the execution of the method does not need to be supervised by human supervision, thereby reducing exploitation costs of the system.

That is, the solution according to the present disclosure allows recording and transmitting images of a display of a monitor acquired in a room of a medical facility, especially in an operating room with reduced disturbances for the practitioners of the room, with reduced or no technical difficulties for the deployment, with reduced or no validation process, without any additional cost, and the solution may eventually provide anonymization of the data and may improve the quality of the original image displayed in the monitor.

The invention claimed is:

1. A computer-implemented method comprising:

obtaining an image of a room of a medical facility, especially an operating room, the image comprising a monitor;

detecting the monitor in the image,;

performing a perspective transformation of the detected monitor in the image for mitigating a perspective distortion of the detected monitor;

anonymizing the image to be transmitted by masking personally identifiable information of a patient;

transmitting an image comprising the detected monitor with mitigated perspective distortion; and wherein anonymizing the image to be transmitted by masking personally identifiable information of a patient comprises:

determining coordinates of the personally identifiable information in the image to be transmitted; and applying a mask on determined coordinates of the image to be transmitted wherein determining coordinates of the personally identifiable information in the image to be transmitted comprises:

applying an optical character recognition method on the image for determining a plurality of characters;

identifying the characters corresponding to the personally identifiable information among the plurality of determined characters; and determining the coordinates associated to the identified characters in the image to be transmitted.

2. The method according to claim 1, wherein determining coordinates of the personally identifiable information in the image to be transmitted comprises:

identifying, in the image to be transmitted, a graphical user interface; and retrieving coordinates associated to the personally identifiable information in the identified graphical user interface.

3. The method according to claim 1, wherein the method further comprises improving a resolution quality of the image to be transmitted based on a super resolution imaging method.

4. A non-transitory computer-readable storage medium comprising instructions which, when executed by at least one controller, cause the at least one controller to carry out a method according to claim 1.

5. A non-transitory computer program product comprising instructions which, when the program is executed by a computer, cause the computer to carry out a method according to claim 1.

6. A system comprising a camera, a controller, a memory, and a communication unit, the system being configured to implement a method according to claim 1.

7. The system according to claim 6, wherein the controller, the memory and the communication unit are incorporated into the camera.

8. The system according to claim 6, further comprising a backpack and a computer, wherein the controller, the memory and the communication unit are incorporated into the computer, and wherein the backpack comprises a first housing sized or shaped to comprise the computer, and a second housing, sized or shaped to comprise the camera.

9. The method according to claim 1, wherein detecting a monitor in the image comprises:

determining a quadrilateral in the image; and wherein the quadrilateral corresponds to the detected monitor.

10. The method according to claim 9, wherein the quadrilateral is determined based on a quadrilateral detection method applied in the image.

11. The method according to claim 9, wherein determining a quadrilateral in the image comprises determining four corners associated to the quadrilateral, and wherein determining the four corners associated to the quadrilateral comprises:

1) receiving four points of the image, acquired by a man-machine interface, identifying the four corners of the quadrilateral corresponding to the four corners of the detected monitor; or 2) identifying four predetermined markers in the image, each of the markers corresponding to a respective corner of the quadrilateral which corresponds to the four corners of the detected monitor.

12. The method according to claim 9, wherein performing a perspective transformation of the detected monitor comprises:

applying a perspective distortion correction method to the quadrilateral corresponding to the detected monitor such that the quadrilateral is transformed to a rectangle.

\* \* \* \* \*